United States Patent [19]

Faulkner

[11] 4,366,582
[45] Jan. 4, 1983

[54] POSTERIOR CHAMBER INTRAOCULAR LENS

[76] Inventor: Gerald D. Faulkner, 1380 Lusitana St., Ste. 714, Honolulu, Hi. 96813

[21] Appl. No.: 211,589

[22] Filed: Dec. 1, 1980

[51] Int. Cl.³ .......................... A61F 1/16; A61F 1/24
[52] U.S. Cl. ........................................................ 3/13
[58] Field of Search ........................................ 3/13, 1

[56] References Cited

U.S. PATENT DOCUMENTS

| 3,994,027 | 11/1976 | Jensen et al. | 3/13 |
| 4,041,552 | 8/1977 | Ganias | 3/13 |
| 4,073,015 | 2/1978 | Peyman et al. | 3/13 |
| 4,092,743 | 6/1978 | Kelman | 3/13 |
| 4,110,848 | 9/1978 | Jensen | 3/13 |
| 4,159,546 | 7/1979 | Shearing | 3/13 |
| 4,242,760 | 1/1981 | Rainin | 3/13 |
| 4,244,060 | 1/1981 | Hoffer | 3/13 |
| 4,285,072 | 8/1981 | Morcher et al. | 3/13 |

Primary Examiner—Ronald L. Frinks
Attorney, Agent, or Firm—Daley & Brandt

[57] ABSTRACT

A lens for implantation in the posterior chamber of the eye is provided with a structure which engages the anterior surface of the iris to retain the lens against posterior displacement within the eye. The lens may be utilized even if the capsule is missing or damaged.

8 Claims, 8 Drawing Figures

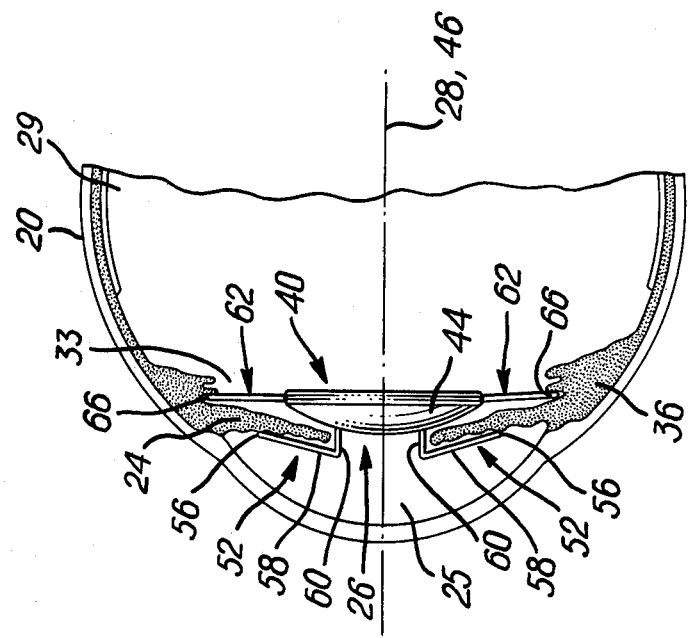
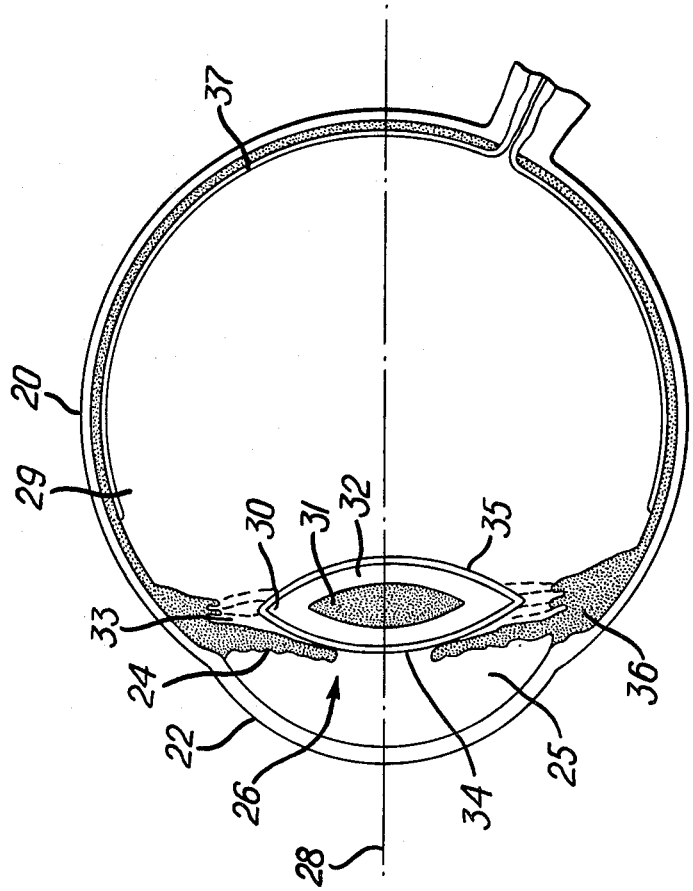
FIG. 2
FIG. 1

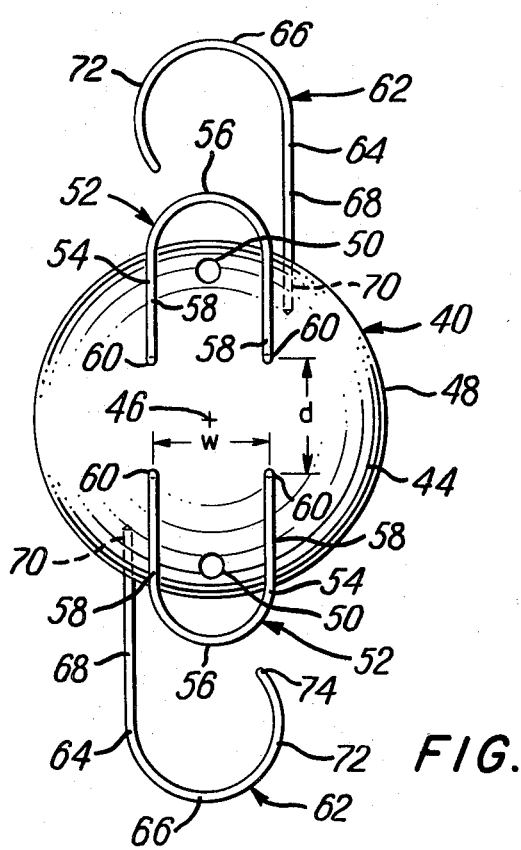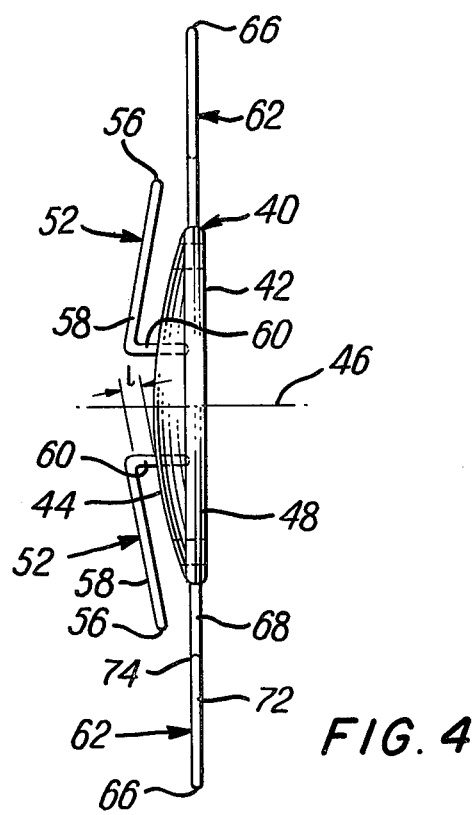
FIG. 3　FIG. 4
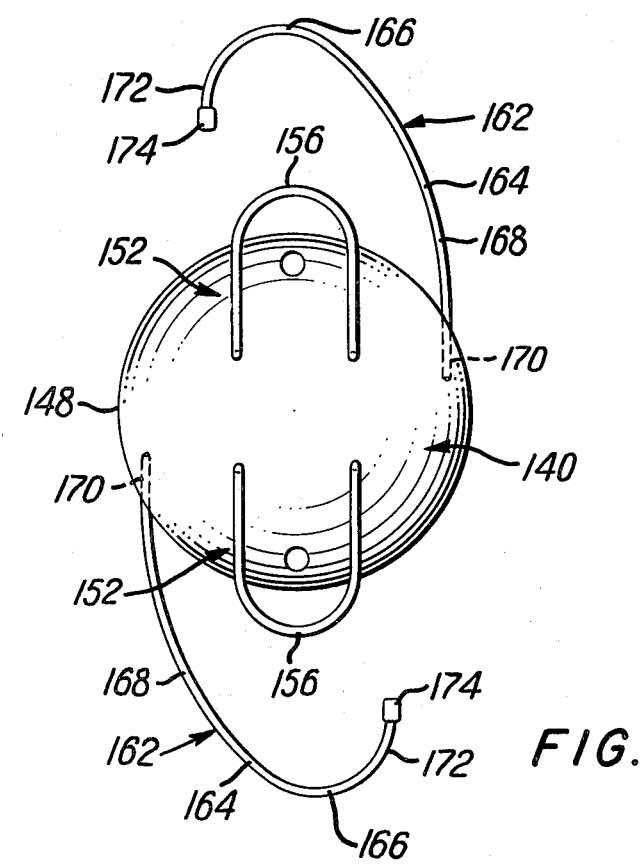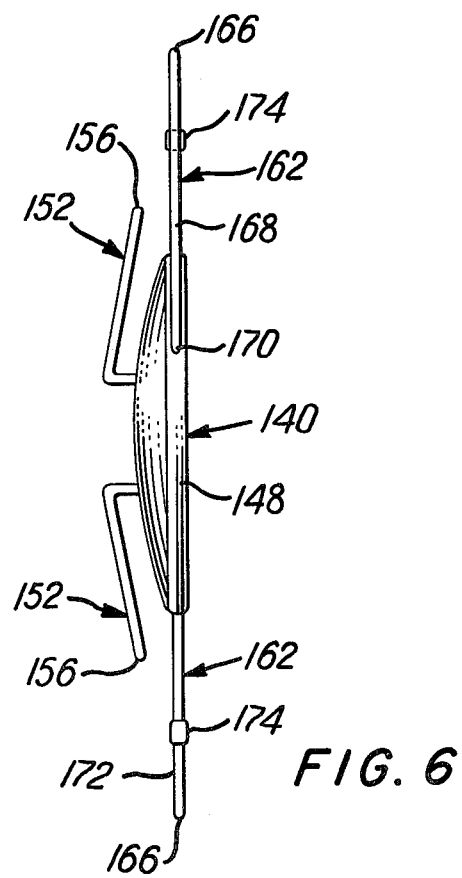
FIG. 5　FIG. 6

POSTERIOR CHAMBER INTRAOCULAR LENS

BACKGROUND OF THE INVENTION

The present invention relates to an intraocular lens for use as a replacement for the natural lens of a human eye.

As an aid in understanding the present invention, background discussion will be given. As illustrated in FIG. 1, a sectional view of a normal eye, the wall 20 of the eyeball has a clear anterior or front portion 22, known as the cornea. The iris 24, a colored annular structure, is disposed posteriorly of cornea 22. The space 25 in front of the iris and behind the cornea is referred to as the anterior chamber. Iris 24 defines a hole or pupil 26 aligned with cornea 22 on the anterior-posterior (front to back) axis 28 of the eyeball. A clear, gelatinous substance known as vitreous is disposed in a cavity 29 posterior of the iris. A lens 30 including a nucleus 31 and a cortex 32 is disposed in the posterior chamber 33, the space between vitreous cavity 29 and iris 24. The lens is surrounded by a capsule consisting of the anterior capsule 34, a clear membrane overlying the anterior surface of lens 30, and the posterior capsule 35, a clear membrane overlying the posterior surface of lens 30, with posterior capsule 35 confronting vitreous cavity 29. Anterior capsule 34 and posterior capsule 35 are connected to the ciliary sulcus 36, a structure on the wall 20 of the eyeball immediately behind iris 24.

In the normal eye, light enters through cornea 22, passes through anterior chamber 25 and pupil 26 and is focused by lens 30 to form an image on retina 37, a light-sensitive tissue lining the rear portion of the eyeball. The retina converts this image into nervous impulses which are transmitted to the brain. The disease known as cataract occurs when either the lens or the capsule becomes clouded or opaque. This interferes with transmission of light to the retina and hence interferes with vision. The only known cure for cataract is to remove the affected tissue. In an "intracapsular" surgical technique, anterior capsule 34, lens 30 and posterior capsule 35 are removed. In an "extracapsular" procedure, only lens 30 and anterior capsule 34 are removed, posterior capsule 35 being left in place within the eye. Many ophthalmologists have been trained only in the intracapsular technique and therefore prefer this technique over the extracapsular technique. The extracapsular technique cannot be utilized if the posterior capsule is diseased or is damaged during surgery.

Once the lens has been removed from the eye, light entering the eye will not be properly focused on the retina without some artificial aid. Such aid can be provided by eyeglasses or contact lenses, but these aids do not provide satisfactory vision correction, comfort and convenience in all cases. Intraocular lenses, which can be surgically implanted within the eye, provide an alternative to eyeglasses and contact lenses.

As generally utilized in the ophthalmologic art, and as utilized herein, the term "intraocular lens" refers to an assembly including both a light focusing element or "optic" and ancillary structures which serve to anchor the optic in place within the eye. Presently available intraocular lenses are commonly categorized as either "anterior chamber," "iris supported" or "posterior chamber." Anterior chamber lenses, designed for placement within the anterior chamber of the eye, ordinarily incorporate rigid supporting structures. When the lens is in place within the eye, such supporting structures are engaged with the eye wall at the juncture of the cornea and the iris to retain the lens in position within the eye. As anterior chamber lenses do not depend upon the capsule to retain them in position within the eye, anterior chamber lenses can be implanted in the eye after an intracapsular extraction procedure, the extraction procedure most familiar to the majority of ophthalmologists. Accordingly, anterior chamber lenses have been widely utilized. However, the rigid supporting structures of anterior chamber lenses must be provided in numerous different sizes to accommodate eyes of various sizes. Moreover, either the optic or the supporting structures of an anterior chamber lens may irritate the cornea.

Iris supported lenses ordinarily incorporate an optic and a plurality of filamentary supports. When the lens is implanted in the eye, the optic is disposed in the anterior chamber, the supports extending through the pupil and radially outwardly along the posterior surface of the iris. Because the iris is engaged between the posterior surface of the optic and the supports, the iris retains the lens in position within the eye. However, this iris can become disengaged from between the optic and the supporting elements upon extreme dilation of the pupil, thus leaving the lens free to move within the eye. In an attempt to alleviate this problem, some iris-supported lenses have been provided with additional supports arranged to extend outwardly from the optic along the anterior surface of the iris. Also, iris-supported lenses have been provided with staves, spikes or sutures extending through the iris to more firmly anchor the optic thereto. Despite such added features, many surgeons prefer to implant iris-supported lenses only when the posterior capsule remains intact within the eye so that scar tissue can firmly attach the supports of the lens to the posterior capsule and anchor the lens in place. This preference, in turn, dictates the employment of an extracapsular procedure for removing the natural lens. This has been an important deterrent to the use of iris-supported lenses. Moreover, if the capsule itself is diseased and must be removed, an extracapsular procedure cannot be utilized. Further, because the optic of an iris-supported lens is positioned in the anterior chamber, the optic can scratch the cornea.

In recent years, posterior chamber lenses have become more widely accepted. The optic of a posterior chamber lens is disposed in the posterior chamber when the lens is implanted. Because the optic is remote from the cornea, the posterior chamber lens generally does not produce corneal irritation. However, the posterior chamber lenses available heretofore have generally depended on the posterior capsule for fixation of the lens within the eye. Accordingly, such lenses have required the use of an extracapsular surgical technique which leaves the posterior capsule intact. For example, the most widely adopted posterior chamber lens heretofore has been the so-called Shearing lens. This lens has two J-shaped resilient support members extending from its optic. The support members engage the wall of the eye of the ciliary sulcus immediately posteriorly of the iris and effectively retain the optic against decentration or movement transversely of the axis of the eye. However, the support members do not provide any substantial support against movement of the optic posteriorly within the eye. Accordingly, the posterior capsule must remain intact if this lens is utilized.

SUMMARY OF THE INVENTION

The present invention provides a posterior chamber intraocular lens which can be adequately anchored within the eye without relying on the capsule for such anchorage. Accordingly, the lens of the present invention can be utilized even if the posterior capsule has been completely removed as by an intracapsular lens extraction procedure, or if the posterior capsule is damaged during surgery.

The present invention also provides an intraocular lens suitable for implantation in eyes of different sizes so that the number of different lenses which must be stocked is minimized. Moreover, the present invention provides a lens which, when implanted in the eye, is retained against posterior dislocation by the iris and retained against decentration by engagement with the wall of the eyeball.

The lens of the present invention preferably includes an optic and support means for engaging an eye structure posterior of the iris to support the optic from such structure and prevent decentration of the optic. Retaining means for engaging the anterior surface of the iris are provided to prevent posterior dislocation of the optic.

The support means may include a radially extensive support structure, which structure may include support elements similar to those employed in the Shearing lens. The retaining means may include a radially extensive retaining structure connected to the optic, such structure being disposed anteriorly of the support structure. When the lens is implanted in the eye, the anterior surface of the optic confronts the posterior surface of the iris and the retaining elements confront the anterior surface of the iris so that the iris is engaged between the anterior retaining elements and the optic. The anterior retaining elements may be flexible and may be formed from filamentary material, such as polypropylene monofilament of the type normally utilized as a surgical suture. Preferably, the anterior retaining elements extend from the anterior surface of the optic. Each anterior retaining element may include a portion extending anteriorly from the juncture of such retaining element with the optic and a radially extensive portion extending from such anteriorly extensive portion. The radially extensive portion of each retaining element may slope posteriorly from its juncture with the anteriorly extensive portion of such retaining element to the tip of the retaining element remote from the optic.

Other objects, features and advantages of the present invention will be more readily apparent from the detailed description of the preferred embodiments set forth below when read in conjunction with the accompanying drawings.

BRIEF DESCRIPTION OF THE DRAWINGS

FIG. 1 is a schematic sectional view of a normal human eye with the natural lens in place.

FIG. 2 is a view similar to FIG. 1 but depicting the anterior portion of the eye with the natural lens removed and an intraocular lens according to a first embodiment of the present invention implanted.

FIG. 3 is an anterior frontal view of the lens depicted in FIG. 2.

FIG. 4 is a lateral elevational view of the lens depicted in FIGS. 2 and 3.

FIGS. 5 and 6 are views similar to FIGS. 3 and 4, respectively, depicting a lens according to a second embodiment of the present invention.

DETAILED DESCRIPTION OF THE PREFERRED EMBODIMENTS

Figure 7:
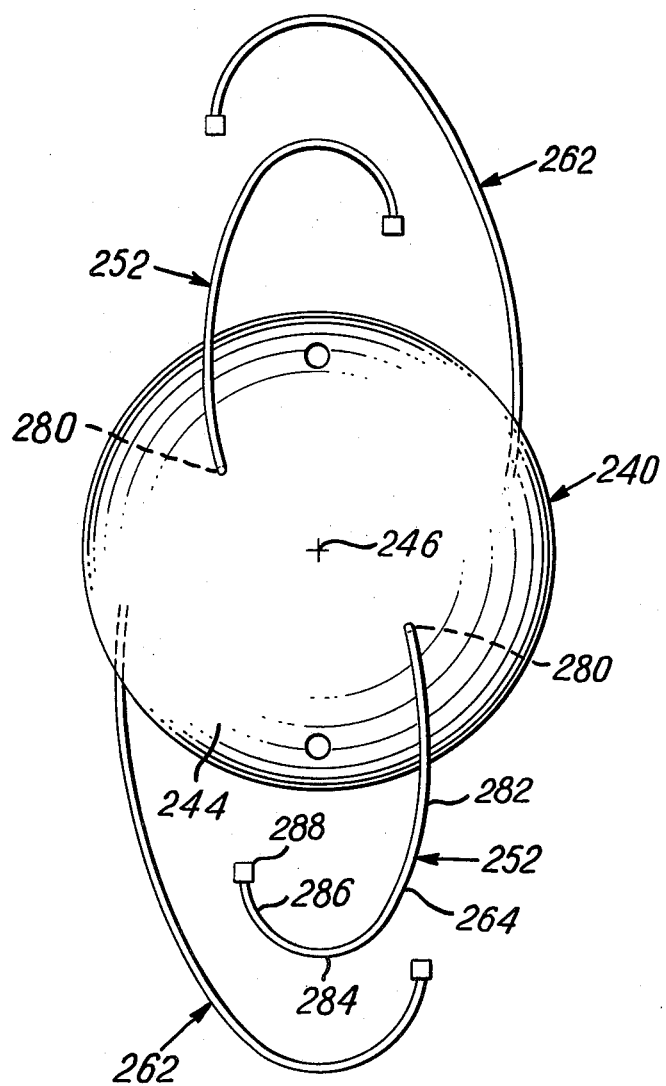
FIGS. 7 and 8 are views similar to FIGS. 3 and 4, respectively, depicting a lens according to a third embodiment of the present invention.

As used herein to describe features of an intraocular lens, the terms "axis," "axial" and "axially" should be understood as referring to the optical axis of the optic, the axis of symmetry of the refractive surfaces of the optic. The terms "radial" and "radially" should be understood as referring to directions transverse to such axis. The term "transaxial plane" should be understood as referring to a plane perpendicular to the axis of the optic. Also, the terms "anterior" and "posterior" as used herein with reference to features of an intraocular lens should be understood as referring to the relative positions and directions of such features in the normal, implanted position of the lens. Thus, for example, if a first feature of the lens is anterior of a second feature, then such first feature will be positioned closer to the front of the eye than the second feature when the lens is implanted. The anterior and posterior directions are directions parallel to the axis of the optic.

As seen in FIGS. 3 and 4, a lens according to a first embodiment of the present invention includes a rigid, disk-like optic 40 having a planar posterior surface 42 and a convex substantially spherical anterior surface 44, anterior surface 44 being symmetrical about axis 46 of optic 40. Optic 40 also has a generally cylindrical peripheral surface 48 concentric with axis 46, peripheral surface 48 extending from anterior surface 44 to posterior surface 42 at the margins thereof. A pair of diametrically opposed holes 50 extend through optic 40 parallel to axis 46.

The lens also includes a pair of retaining elements 52, such retaining elements being substantially identical with one another. Each retaining element consists solely of a single filament 54, each such filament being configured generally in the shape of a U. The bight of each filament which forms the base of the U defines the tip 56 of the retaining element remote from axis 46. The portions 58 of each filament 54 defining the legs of the U extend generally radially. At the extremities of such portions remote from tip 56, each filament is bent out of the plane of the U. As best seen in FIG. 4, portions 60 of the filament extend from the leg portions 58 through the anterior surface 44 of optic 40, the tips of portions 60 being imbedded in optic 40. In other words, portions 60 of each retaining element extend anteriorly (to the left as seen in FIG. 4) from the anterior surface 44 of optic 40, and the remainder of each retaining element extends radially outwardly from its juncture with anteriorly extending portions 60 of such retaining element to its tip 56. As will be apparent from FIG. 4, the radially extensive portion of each retaining element slopes posteriorly (towards the right in FIG. 4) from its juncture with the anteriorly extensive portions 60 to tip 56. The two retaining elements 52 are diametrically opposed to one another. That is, a line drawn between the tips 56 would cross axis 46.

Two support elements 62 are provided. Each support element is formed solely from a single filament 64 configured generally in the shape of a J. The bight of each filament defining the base of the J forms the tip 66 of support element 62 remote from axis 46 to optic 40. The portion of each filament 64 defining the stem 68 of the J extends generally radially, the end 70 of each such portion remote from tip 66 extending through peripheral wall 48 of optic 40. Each such end is imbedded in optic 40. The portion 72 of each filament 64 defining the hook of the J extends from tip 66 of the support element towards optic 40, but the ends 74 of portions 72 are not imbedded in optic 40. Because ends 74 are exposed, they are preferably rounded or otherwise blunted.

As best seen in FIG. 4, support elements 62 are disposed in a common transaxial plane and are posterior of retaining elements 52. Support elements 62 are diametrically opposed to one another; a line drawn between the tips 66 of support elements would intercept axis 46. Also, each retaining element 52 is aligned with one of the support elements 62. When the lens is viewed in a frontal projection such as FIG. 3, a radius drawn from axis 46 to the tip 56 of each retaining element 52 would appear closely adjacent to a radius drawn from axis 46 to the tip 66 of the support element aligned with such retaining element.

As seen in FIG. 2, optic 40 is disposed in posterior chamber 33 when the lens is implanted in the eye. Portions of anterior surface 44 of the optic confront the posterior surface of iris 24. Axis 46 of optic 40 is substantially coincident with the anterior-posterior axis 28 of the eye. Tips 66 of support elements 62 are engaged with the ciliary sulcus 36 of the eye and support optic 40 therefrom. The anteriorly extending portions 60 of retaining elements 52 extend through pupil 26 and the radially extensive portions 58 of the retaining elements overlie the anterior surface of iris 24. Thus, the retaining elements prevent dislocation or movement of optic 40 in the posterior direction (to the right as seen in FIG. 2) into vitreous chamber 29. Because optic 40 is retained against decentration (displacement away from the axis 28 of the eye) by support elements 62, retaining elements 52 need not engage the iris in such fashion as to resist decentration loads.

Support elements 62 are ordinarily flexed slightly inwardly towards axis 46 from the free or undeformed positions illustrated in FIGS. 3 and 4 when they are engaged with the ciliary sulcus 36. The dimensions, configuration and material of construction of support elements 62 are selected so that when the support elements are engaged with the ciliary sulcus, the support elements will exert a mild pressure on the ciliary sulcus sufficient to retain the support elements in engagement but insufficient to irritate the eye tissues. The open, J-shaped configuration of the support elements, best seen in FIG. 3, allows the support elements to deflect radially inwardly over a wide range of positions with only minimal variations in the force which they exert on the eye tissues. Accordingly, the J-shaped support elements can be engaged with eyes of different sizes.

Support elements 62 may be formed from any biologically and structurally suitable material, including polypropylene, polyamide or platinum, polypropylene being preferred. If each support element 62 is formed from a single filament of polypropylene, each such filament is preferably about 0.14 to 0.17 mm. in diameter. The diameter across the tips 66 of the support elements (the diameter of the smallest circle concentric with axis 46 which completely encloses support elements 62 in their free or undeformed state) is preferably about 13 mm.

Retaining elements 52 are less flexible than support elements 62. The diameter across the retaining elements (the diameter of the smallest circle concentric with axis 46 which will completely enclose the retaining elements in their free or undeformed state) is less than the major diameter of the normal iris. Therefore, tips 56 of the retaining elements do not contact the wall of the eye, and the retaining elements need not deform radially inwardly to accommodate eyes of different sizes. Preferably, the diameter across the retaining elements is about 7.75 mm. The width w (FIG. 3) of each retaining element is preferably about 2.0 mm. and the distance d between the two opposed retaining elements across the center of the lens is also preferably about 2.0 mm. The radially extensive portions 58 of the retaining elements preferably slope posteriorly at an angle of between about 5° and about 15°, that is, the angle between each such radially extensive portion and a transaxial plane is about 5° to about 15°. The length l (FIG. 4) of each of the anteriorly extending portions 60 of the retaining elements 52, as measured from its intersection with the radially extensive portion of such retaining element to its intersection with anterior surface 44 of optic 40, is preferably between about 0.30 and about 0.43 mm. This arrangement provides appropriate spaces between the retaining elements and the optic, and between the retaining elements and the support elements, for insertion of the iris.

The retaining elements can be formed from any of the materials referred to above in connection with the support elements, polypropylene being the preferred material. If each retaining element is formed from a single filament of polypropylene, each such filament is preferably about 0.17 to 0.21 mm. in diameter.

Optic 40 may be formed from any material having suitable optical, structural and biological properties. Polymethylmethacrylate is preferred. Optic 40 may be about 6.0 mm. in diameter. The thickness of the optic, and the precise shape of its anterior surface, will be selected to provide the appropriate refractive effect for the particular eye.

One suitable technique for implanting the lens described above in the eye is as follows:

1. Remove the natural lens of the eye by conventional surgical procedure, leaving a wound opening in the wall of the eyeball adjacent to the top of the eye just anteriorly of the iris.

2. Clear the anterior chamber of any vitreous material until a single air bubble fills the chamber and there is no distortion of the pupil by strands of vitreous material.

3. Maintain the shape of the anterior chamber.

4. Adjust the size of the wound opening to between about 7.0 mm. and about 8.0 mm.

5. Insert a lens glide carefully through the wound and through the pupil so that the inserted end of the lens glide is behind the iris and positioned at the bottom or inferior portion of the eye.

6. Use acetyl choline chloride if necessary to adjust the diameter of the pupil to less than 6.0 mm.

7. Grasp the retaining elements with a smooth McPherson forceps so that the jaws of the forceps are parallel to the retaining elements and support elements. Hold the forceps so that one support element is lower than the other.

8. Lift the cornea with one hand to clear the retaining elements while inserting the lower support element and the optic along the glide. Press gently on the glide in a posterior direction while passing the optic into the anterior chamber of the eye and insert the lower support element and the lower portion of the optic through the pupil. Engage the iris between the lower portion of the optic and the lower retaining element.

9. Continue to hold the cornea and remove the forceps from the retaining elements. Grasp the upper support element, compress it slightly and place it just inside the eye anteriorly of the iris at the juncture of the iris and the eye wall at the top of the eye. Release the upper support element so that it lodges in the angle between the iris and the eye wall, and check if the lens remains in place. If it does, this indicates that the support elements are of sufficient size to properly engage the eye wall.

10. Pass a Bonn hook beneath the lens and retract the pupil at about the 1:30 o'clock position. Insert a Sinskey hook into the operculum adjacent the top of the lens and pivot the top portion of the lens posteriorly while exerting slight inferior and posterior pressure until the upper support element is disposed posteriorly of the iris and the iris is disposed between the optic and the upper retaining element.

11. Using a hook or forceps, lift the lens gently and rock it along the axis of the support elements to assure that the tips of the support elements are engaged in the ciliary sulcus.

12. Perform a peripheral iridectomy or iridotomy.

13. If desired, a suture may be placed through the iris and around one of the retaining elements.

14. Close the wound.

A lens according to a second embodiment of the present invention is depicted in FIGS. 5 and 6. The optic 140 and retaining elements 152 of this lens are similar to the optic 40 and retaining elements 52 of the lens described above with reference to FIGS. 3 and 4. The support elements 162 of the lens shown in FIGS. 5 and 6 are J-shaped, but the stems 168 of such support elements are curved rather than straight. The ends 170 of stems 168 intersect peripheral surface 148 of optic 140 almost tangentially as seen in FIG. 5. The diameter across the support elements 162 is between about 13.35 and about 13.65 mm. when the supporting elements are in their free or undeformed state. Each of the support elements 162 is formed from a polypropylene filament 164 between about 0.14 and 0.17 mm. in diameter. The end 174 of each support element filament 164 at the extremity of the hook portion 172 of such support element is formed into a blunt knob slightly thicker than the diameter of the filament. The term "blunt" as used herein refers to a structure which is devoid of sharp edges which might irritate eye tissues.

Figure 8:
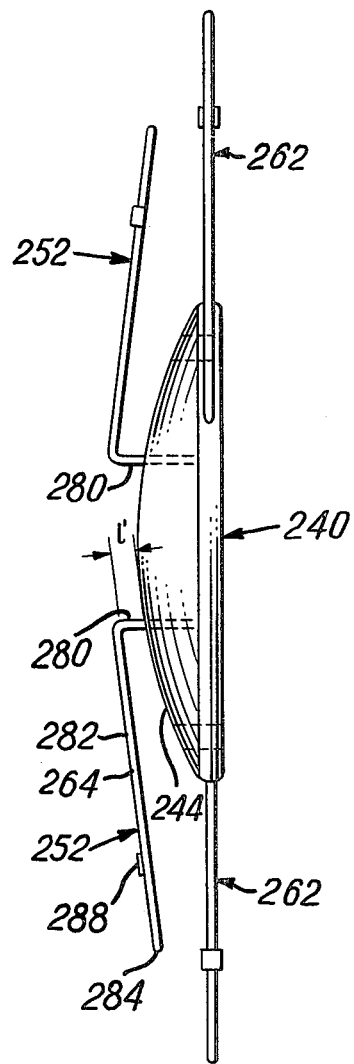

A lens according to a third embodiment of the present invention is depicted in FIGS. 7 and 8. This lens incorporates an optic 240 and support elements 262 similar to the optic and support elements of the lens described above with reference to FIGS. 5 and 6. The retaining elements 252 of the lens depicted in FIGS. 7 and 8 are J-shaped rather than U-shaped. Each retaining element 252 is formed from a single polypropylene filament 264 and incorporates a single anteriorly extensive portion 280 which intersects anterior surface 244 of optic 240. A curved stem portion 282 extends generally radially from its intersection with anteriorly extensive portion 280 to bight 284 which forms the tip of the retaining element. Each such radially extensive portion 282 slopes posteriorly from its intersection with anteriorly extensive portion 280 towards tip 284. A portion 286 of each retaining element filament extends back towards optic 240 from tip 284 so that portion 286 at hook defining portion 286 is remote from optic 240 and is not engaged therewith. Rather, a blunt knob 288 is formed at such end of the filament. As best seen in FIG. 8, each knob 288 projects anteriorly of the filament but does not project posteriorly thereof. Therefore, knobs 288 will not engage the iris when the lens is implanted in the eye.

The length l' of each anteriorly extensive portion 280 is preferably about 0.4 mm. as measured from its intersection with optic anterior surface 244 to its intersection with the associated stem portion 282. Each stem portion 282 preferably slopes posteriorly from its intersection with anteriorly extensive portion 280 at an angle of between about 3° and about 5°, although any angle of posterior slope greater than 0° may be utilized, and angles of more than 5° may be utilized if the lens is especially thick. However, the anterior to posterior distance from the tip 284 of each retaining element to the plane of the support elements should not be less than about 0.5 mm. or more than about 0.8 mm.

If the retaining elements 252 are formed from polypropylene filaments, such filaments are preferably about 0.14 to 0.17 mm. in diameter. As each retaining element 252 is engaged with optic 240 at only one end, retaining elements 252 are significantly more flexible in the radial direction that the retaining elements of the lenses described above with reference to FIGS. 3 through 6. Preferably, the diameter across the retaining elements 252 in their free or undeformed state is about 10.5 mm. Thus, tips 284 of the retaining elements extend far enough from the axis 246 of the optic so that when the lens is implanted in a normal human eye tips 284 will extend to the periphery of the iris and engage the wall of the eyeball. Thus, retaining elements 284 may provide additional support against decentration of optic 240. However, because retaining elements 252 are quite flexible in the radial direction, they can accomodate different eye sizes and they will not exert undue pressure against the wall of the eye. Also, because retaining elements 252 extend all the way to the periphery of the iris, they may provide greater security against disengagement upon dilation of the pupil, and hence may provide greater security against posterior dislocation of the optic.

Lenses according to the present invention have given good results in trial implantations. The first such lens was implanted in an instance where a rupture of the posterior capsule was suspected. Observation of the first eye for three months revealed good results. Further implants for this type of condition were carried out on six patients. The patients were observed during follow-up periods after implantation in accordance with normal investigational practice. These patients had very good results considering that rupture of the capsule often creates susceptibility to other complications. The results of these trial implantations are summarized in Table I below.

TABLE I

| Patient | Age/Sex | Vitreous Loss | Visual Acuity at Last Follow-up | Follow-up Period After Implantation | Notes |
|---|---|---|---|---|---|
| 1 | 69/F | NO | 20/30 | 12 Months | |
| 2 | 68/M | YES | 20/30 | 9 Months | |
| 3 | 88/F | YES | 20/25 | 4 Months | |
| 4 | 68/F | NO | 20/20 | 4 Months | 1. |
| 5 | 73/M | YES | 20/20 | 3 Months | |
| 6 | 52/M | YES | 20/20 | 3 Months | 2. |

TABLE I-continued

| Patient | Age/ Sex | Vitreous Loss | Visual Acuity at Last Follow-up | Follow-up Period After Implantation | Notes |
|---|---|---|---|---|---|
| 7 | 80/F | YES | 20/40 | 3 Months | 3. |

NOTES:
1. Capsule disinsertion — required capsulotomy at two months.
2. Retained cortex in vitreous cleared at two months.
3. Nuclear fragment in vitreous removed from anterior chamber two weeks post op. and lens inserted.

Lenses according to the present invention also were used in patients who had had an intracapsular cataract operation at some time prior to implantation. Five of these implantations were performed with good results, summarized in Table II.

TABLE II

| Pa- tient | Age/ Sex | Vitreous Loss | Visual Acuity at Last Follow-up | Follow-up Period After Implantation | Notes |
|---|---|---|---|---|---|
| 8 | 87/F | PLANNED | 20/40 | 3 Months | 1. |
| 9 | 73/F | NO | 20/40 | 2 Months | 2. |
| 10 | 57/M | YES | 20/25 | 6 Months | 3. |
| 11 | 76/M | NO | 20/20 | 2 Months | |
| 12 | 66/M | NO | 20/20 | 2 Months | |

NOTES:
1. Residual astigmatism 5 diopters.
2. Small vitreous herniation into anterior chamber.
3. Lens exchange — loose 3 loop Binkhort lens.

As will be readily appreciated, numerous variations and combinations of the features described above can be utilized without departing from the present invention. Merely by way of example, the retaining elements need not be aligned with the support elements as in the embodiments described above. Also, additional retaining elements, additional support elements, or both, may be provided. As these and other variations may be utilized, the foregoing description of the preferred embodiments should be understood by way of illustration rather than by way of limitation of the present invention as defined in the claims.

What is claimed is:
1. A posterior chamber intraocular lens comprising:
   (a) an optic;
   (b) support means for engaging an eye structure posterior of the iris to support said optic from said eye structure and retain said optic in alignment with the anterior-posterior axis of the eye, said support means including radially extensive support structure connected to said optic; and
   (c) retaining means for engaging the anterior surface of the iris to impede posterior dislocation of said optic, said retaining means including a plurality of radially extensive retaining elements each of which is connected to said optic, said retaining elements being disposed at circularly spaced locations about the axis of said optic and anteriorly of said support structure, each of said retaining elements including an elongated filament one end of such filament being embedded in said optic with the other end constituting a tip of the retaining element defined by a bight in the filament included in such element, each of said retaining elements being formed solely from one of said filaments in the shape of a J with the base of such J being remote from said optic, the non-embedded ends of said J-shaped filaments being devoid of sharp edges, the diameter across said retaining elements being such that the tips of said retaining elements are adapted to extend to the periphery of the normal human iris and engage the wall of the eyeball.

2. A lens as claimed in claim 1 in which the diameter across said retaining elements is about 10.5 mm.

3. A lens as claimed in claim 2 in which each of the filaments constituting one of said retaining elements is a polypropylene filament about 0.14 to 0.17 mm. in diameter.

4. A lens as claimed in claim 1 having two diametrically opposed retaining elements, each J-shaped retaining element having a curved stem part connecting the base of the J with the optic.

5. A lens as claimed in claim 1 in which the support means comprises two diametrically opposed elongated J-shaped support filaments each having an end thereof embedded in the optic with its other end constituting a tip of the supporting filament, the base of the J being remote from said optic, the non-embedded ends of said support filaments being devoid of sharp edges.

6. A lens as claimed in claim 5 in which each of said retaining elements is aligned with a corresponding one of said support filaments.

7. A lens as claimed in claim 5 in which the base of the J of each supporting filament is more remote from the optic than the base of the J of each retaining element.

8. A lens as claimed in claim 5 in which the non-embedded ends of said retaining element filaments and said support filaments are provided each with blunt knobs thicker than the diameter of the respective filaments, the knobs on said retaining element filaments projecting anteriorly of the filament but having no parts thereof projecting posteriorly of the filament.

* * * * *